US00PP29501P3

(12) United States Plant Patent
Bacon

(10) Patent No.: US PP29,501 P3
(45) Date of Patent: Jul. 17, 2018

(54) GRAPEVINE PLANT NAMED 'SUGRAFIFTYONE'

(50) Latin Name: *Vitis vinifera*
Varietal Denomination: Sugrafiftyone

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 92 days.

(21) Appl. No.: 15/330,450

(22) Filed: Sep. 22, 2016

(65) Prior Publication Data

US 2018/0084687 P1 Mar. 22, 2018

(51) Int. Cl.
*A01H 5/08* (2018.01)

(52) U.S. Cl.
USPC ..... Plt./207
CPC ..... *A01H 5/0812* (2013.01)

(58) Field of Classification Search
USPC ..... Plt./207
See application file for complete search history.

*Primary Examiner* — Anne Marie Grunberg
(74) *Attorney, Agent, or Firm* — Knobbe, Martens, Olson & Bear, LLP

(57) ABSTRACT

A new and distinct variety of grapevine 'Sugrafiftyone' is characterized by early harvest date, the production of a large-sized, green, obtuse-ovoid berry and a large bunch size. The berries of 'Sugrafiftyone' are very firm.

1 Drawing Sheet

Latin name of the genus and species claimed: *Vitis vinifera.*

Variety denomination: 'SUGRAFIFTYONE'.

BACKGROUND AND SUMMARY OF THE INVENTION

This application relates to the discovery and asexual propagation of a new and distinct variety of grapevine, 'Sugrafiftyone', as herein described and illustrated. The new variety was first selected as breeder number 'GR366W' by Terry A. Bacon in Wasco, Kern County, Calif. in July 2013. The variety was originated by controlled hybridization.

The new variety 'Sugrafiftyone' is characterized by early harvest date, the production of a large-sized, green, obtuse-ovoid berry and a large bunch size. The berries of 'Sugrafiftyone' are very firm.

The seed parent is the varietal selection 'Sugrafortytwo' (U.S. Plant Pat. No. 24,250) and the pollen parent is '06100-049-397' (unpatented). The parent varieties were first crossed in May 2010. The date of first sowing was March 2011, and the date of first flowering was May 2012.

The new variety 'Sugrafiftyone' was first asexually propagated in December 2013 in Wasco, Kern County, Calif., by Terry A. Bacon using hardwood cuttings.

The new variety 'Sugrafiftyone' differs from its seed parent 'Sugrafortytwo' (U.S. Plant Pat. No. 24,250) in that harvest of grapes of the new variety 'Sugrafiftyone' starts about 12 days earlier at about July 14th compared to about July 24th for 'Sugrafortytwo'. The new variety 'Sugrafiftyone' also differs from its seed parent 'Sugrafortytwo' in that the new variety 'Sugrafiftyone' has a larger berry at about 8.5 g while 'Sugrafortytwo' has a smaller berry at about 6.7 g. The new variety 'Sugrafiftyone' is similar to its seed parent 'Sugrafortytwo' in that both have a green berry.

The new variety 'Sugrafiftyone' differs from its pollen parent '06100-049-397' (unpatented) in that ripening of grapes of the new variety 'Sugrafiftyone' starts about 2 months earlier at about July 14th compared to about September 15 for '06100-049-397'. The new variety 'Sugrafiftyone' also differs from its pollen parent '06100-049-397' in that the new variety 'Sugrafiftyone' has a larger berry at about 8.5 g while '06100-049-397' has a smaller berry at about 6 g. The new variety 'Sugrafiftyone' is similar to its pollen parent '06100-049-397' in that both have a green berry.

The new variety 'Sugrafiftyone' has similar berry color and harvest starts at about the same time as 'Sugraone' (U.S. Plant Pat. No. 3,106), but the new variety cluster size is larger at about 800 g compared to about 625 g for 'Sugraone', and the new variety berry size is larger at about 8.5 g compared to about 7.5 g for 'Sugraone'. The berry color of the new variety 'Sugrafiftyone' is similar to 'Thompson Seedless' (unpatented) but the new variety berry shape is obtuse-ovoid, compared to elongated for 'Thompson Seedless'. The new variety 'Sugrafiftyone' has a green berry color, compared to a red berry color for 'Scarlet Royal' (U.S. Plant Pat. No. 16,229) and a black berry for 'Sugrathirteen' (U.S. Plant Pat. No. 10,434). Harvest of the new variety 'Sugrafiftyone' starts earlier than 'Scarlet Royal' and 'Sugrathirteen' and the new variety has a larger cluster and berry weight.

The new 'Sugrafiftyone' variety has been shown to maintain its distinguishing characteristics through successive asexual propagations by, for example, cuttings, and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration shows typical specimens of the foliage and fruit of the present new grape variety 'Sugrafiftyone'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three year old 'Sugrafiftyone' plants grown in the vicinity of Wasco, Kern County, Calif. during 2016, and is believed to apply to plants of the variety grown under similar conditions of soil and climate elsewhere.

VINE

General: (Measurements taken on a three year old plant).

- *Vine size*.—Large. Height: Approximately 2.0 m. Width: Approximately 2.5 m.
- *Vigor*.—Vigorous.
- *Density of foliage*.—Dense.
- *Productivity*.—Very productive.
- *Crop load*.—Approximately 30 kg per vine after thinning.
- *Own root*.—Yes.
- *Training method*.—Typically spur pruned leaving 2 bud spurs.
- *Resistance*.—Neither resistance nor susceptibility to diseases or pests has been observed in this variety.

Trunk:

- *Shape*.—Stocky.
- *Diameter*.—Approximately 7.5 cm (at 30 cm above the soil line).
- *Straps*.—Short.
- *Surface texture*.—Medium shaggy.
- *Inner and outer bark color*.—Inner bark about Medium Greyed-Orange 173C and Medium Greyed-Green 188B in outer bark.

SHOOTS

Young shoot:

- *Form of tip*.—Slightly open.
- *Intensity of anthocyanin coloration of tip*.—Absent or very weak.
- *Density of prostrate hairs on tip*.—Medium.
- *Density of erect hairs on tip*.—Absent or very sparse.
- *Color*.—About Medium Yellow-Green 146D.

Woody shoot (observations made in the middle third of the shoot):

- *Attitude before tying*.—Semi-drooping to drooping.
- *Growth of axillary shoots*.—Medium strong, approximately 170 mm to 300 mm.
- *Internode length*.—Medium, Approximately 65 mm.
- *Width at node*.—Approximately 15 mm.
- *Cross section*.—Circular.
- *Surface texture*.—Striated.
- *Main color*.—About Medium Greyed-Orange 166B.
- *Color of dorsal side of internode*.—About Medium Greyed-Orange 166B.
- *Color of ventral side of internode*.—About Medium Greyed-Orange 166B.
- *Color of dorsal side of node*.—About Medium Yellow-Green 146C with Medium Greyed-Orange 166B.
- *Color of ventral side of node*.—About Medium Yellow-Green 146C with Medium Greyed-Orange 166B.
- *Density of erect hairs on nodes*.—Absent or Very Sparse.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—Approximately 4 mm.
- *Color*.—About Light Yellow-Green 148D in mid-summer.
- *Form*.—Bifurcated.
- *Number of consecutive tendrils*.—Up to 2.
- *Length of tendril*.—Medium, approximately 16.5 cm.

LEAVES

Young leaves:

- *Color of upper surface of first* 4 *distal unfolded leaves*.—About Medium Yellow-Green 144B.
- *Average intensity of anthocyanin coloration of six distal leaves prior to flowering*.—Absent.
- *Density of prostrate hairs between veins at lower surface of* 4*th distal unfolded leaf*.—Absent or very sparse.
- *Density of erect hairs between veins at lower surface of* 4*th distal unfolded leaf*.—Absent or very sparse.
- *Density of prostrate hairs on veins at lower surface of* 4*th distal unfolded leaf*.—Absent or very sparse.
- *Density of erect hairs on veins at lower surface of* 4*th distal unfolded leaf*.—Absent or very sparse.

Mature leaves (observations made in the middle third of the shoot):

- *Average length*.—Large, approximately 13 cm.
- *Average width*.—Large, approximately 13 cm.
- *Shape of blade*.—Pentagonal.
- *Number of lobes*.—Approximately 5.
- *Mature leaf profile*.—Undulate.
- *Blistering surface of blade upper surface*.—Absent or very weak.
- *Leaf blade tip*.—In the plane of the leaf.
- *Undulation of margin*.—Slight.
- *Thickness*.—Average — typical of *Vitis vinifera* species.
- *Overall shape of teeth*.—Mixture of both sides straight and both sides convex.

*Length of teeth*.—Medium, ranging from about 5 mm to 12 mm.
*Ratio length/width of teeth*.—Very small.
*General shape of petiole sinus lobes*.—Wide open.
*Tooth at petiole sinus*.—Absent.
*Petiole sinus limited by veins*.—Absent.
*Shape of upper lateral sinus lobes*.—Closed to slightly overlapping.
*Depth of upper lateral sinuses*.—Medium, approximately 40 mm to 50 mm.
*Density of prostrate hairs between veins on lower surface of blade*.—Absent to very sparse.
*Density of erect hairs between veins on lower surface of blade*.—Absent to very sparse.
*Density of prostrate hairs on main veins on lower surface of blade*.—Absent to very sparse.
*Density of erect hairs on main veins on lower surface of blade*.—Absent to very sparse.
*Density of prostrate hairs on main veins on upper surface of blade*.—Absent to very sparse.
*Autumn coloration of leaves*.—Mostly about Light Yellow-Green 154C.

Upper leaf surface:
*Color*.—About Medium Green 137C.
*Surface texture*.—Smooth.
*Surface appearance*.—Dull.
*Anthocyanin coloration of main veins*.—Absent or very sparse.

Lower leaf surface:
*Color*.—About Medium Green 138B.
*Surface texture*.—Smooth.
*Surface appearance*.—Dull.
*Anthocyanin coloration of main veins*.—Absent or very sparse.

Petiole:
*Length of petiole*.—Medium, approximately 8 cm to 10 cm, mainly 9 cm.
*Diameter*.—Approximately 3 mm.
*Length of petiole compared to middle vein*.—Slightly shorter, 9 cm for the petiole compared to 13 cm for middle vein.
*Density of prostrate hairs on petiole*.—Absent.
*Density of erect hairs on petiole*.—Absent.
*Color*.—About Medium Green 138B becoming Medium Greyed-Red 179B as it ages.

Buds:
*Shape*.—Conical.
*Size*.—Medium, approximately 3 mm wide×4 mm long.
*Position*.—Slightly held out.
*Bud fruitfulness*.—Basal, mostly fruitful $3^{rd}$ to $5^{th}$ bud position.
*Time of bud burst*.—Medium for area of Wasco, Calif. Approximately March 10th.

FLOWERS

General:
*Flower type*.—Fully developed stamen and fully developed gynoecium.
*Position of first flowering node*.—Usually $3^{rd}$ to $5^{th}$ node of current season growth.
*Number of inflorescences per shoot*.—Approximately 1 to 2 with an average of about 1.5.
*Time of full bloom*.—Medium for the area of Wasco, Calif. Approximately April 30th.

FRUIT

General:
*Ripening period*.—Early, beginning about July $14^{th}$ with mid-ripe about July 19.
*Use*.—Fresh market.
*Storage quality*.—Excellent, at least 6 weeks.

Cluster:
*Form*.—Conical, shouldered.
*Cluster size* (*peduncle excluded*).—Large.
*Cluster length* (*peduncle excluded*).—Approximately 21 cm.
*Cluster width*.—Approximately 15 cm.
*Cluster weight*.—Approximately 800 g.
*Cluster density*.—Medium, loose and full.
*Number of berries*.—Approximately 100-120.

Peduncle:
*Length*.—Medium, approximately 2.2 cm.
*Diameter*.—Approximately 6 mm.
*Lignification of peduncle*.—Weak.
*Color*.—About Light Green 138C.

Berry:
*Size*.—Very large, natural size averages 8.5 g.
*Dimensions*.—Longitudinal axis: Approximately 33 mm. Horizontal axis: Approximately 24 mm.
*Uniformity of size*.—Uniform.
*Shape*.—Obtuse-ovoid.
*Cross section*.—Circular.
*Skin color* (*without bloom*).—About Light Yellow-Green 147D.
*Flesh color*.—About Light Yellow-Green 147D.
*Anthocyanin color of flesh*.—Absent.
*Bloom* (*cuticular wax*).—Medium, typical for most commercial table grapes.
*Pedicel length*.—Medium, Approximately 1.7 mm.
*Pedicel thickness*.—Approximately 7 mm.
*Berry separation from pedicel*.—Moderately easy.
*Seed traces*.—Berries contain 1 to 3 rudimentary soft seed traces per berry. Seed traces are about Medium Greyed-White 156B.
*Berry firmness*.—Very firm.
*Flesh juiciness*.—Juicy.
*Flesh texture*.—Crisp.
*Particular flavor*.—Slightly muscat when mature.
*Refractometer test*.—About 18 Brix.
*Juice ph*.—About 3.6.
*Titratable acidity*.—About 0.49%.
*Brix:acid ratio*.—Approximately 38.8.

Skin:
*Skin thickness*.—Medium, about 175 μm.
*Skin texture*.—Smooth.
*Skin reticulation*.—Absent.
*Skin tenacity*.—Tenacious to flesh.
*Skin tendency to crack*.—Low.
*Skin sensitivity to sunburn*.—None or very low.

What is claimed is:

1. A new and distinct variety of grapevine as herein illustrated and described.

* * * * *

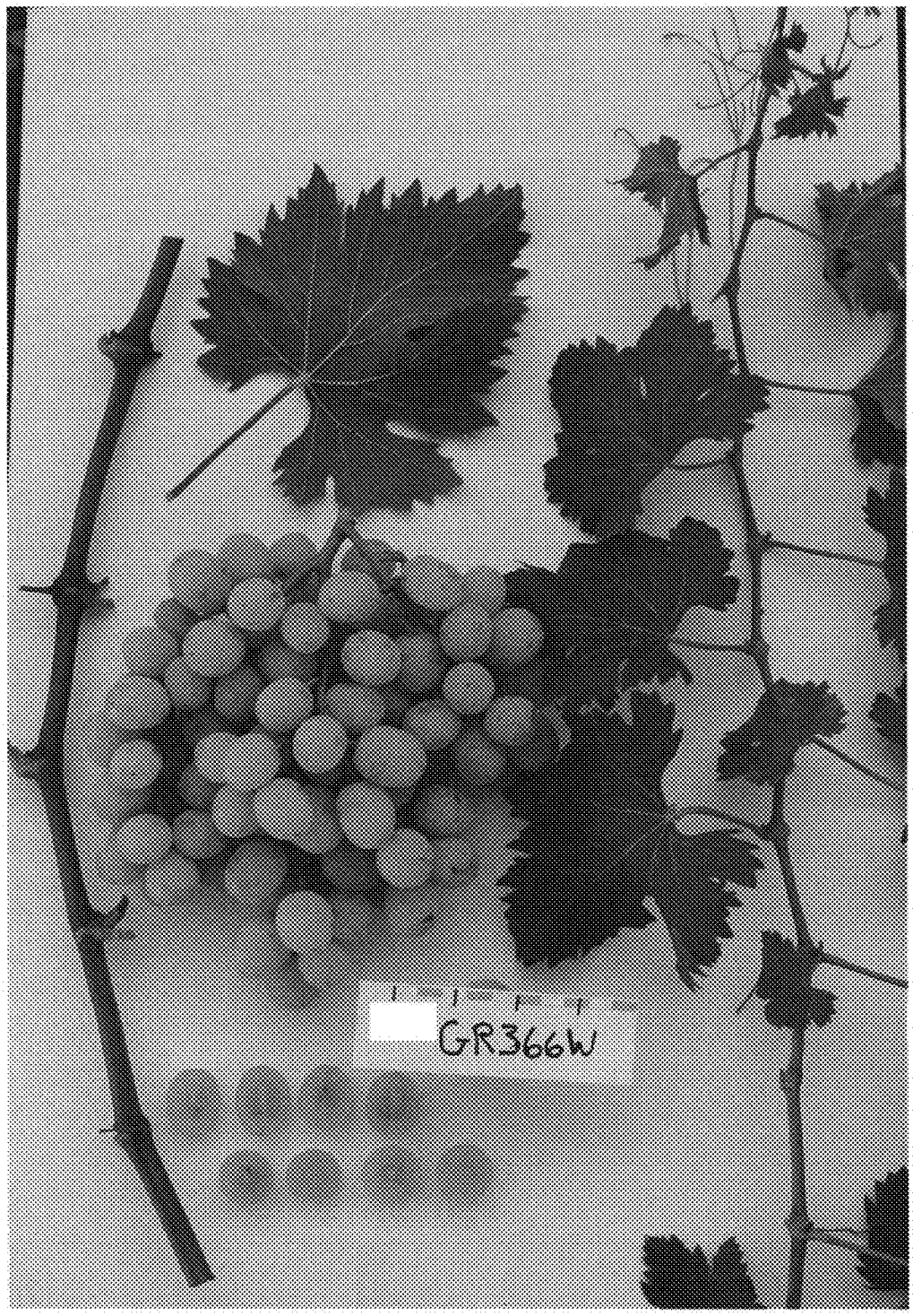
GR366W